(12) United States Patent
Chappa (10) Patent No.: US 8,142,836 B2
(45) Date of Patent: Mar. 27, 2012

(54) MULTI-LAYERED COATINGS AND METHODS FOR CONTROLLING ELUTION OF ACTIVE AGENTS

(75) Inventor: Ralph A. Chappa, Ham Lake, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

(21) Appl. No.: 12/885,801

(22) Filed: Sep. 20, 2010

(65) Prior Publication Data

US 2011/0008526 A1   Jan. 13, 2011

Related U.S. Application Data

(63) Continuation of application No. 11/860,856, filed on Sep. 25, 2007, now abandoned.

(60) Provisional application No. 60/826,823, filed on Sep. 25, 2006.

(51) Int. Cl.
*A61K 9/38* (2006.01)
*A61F 2/00* (2006.01)

(52) U.S. Cl. ........................ 427/2.14; 424/426

(58) Field of Classification Search .................. None
See application file for complete search history.

(56) References Cited

U.S. PATENT DOCUMENTS

| | | | |
|---|---|---|---|
| 4,123,308 A | 10/1978 | Nowlin et al. |
| 4,638,045 A | 1/1987 | Kohn et al. |
| 5,002,582 A | 3/1991 | Guire et al. |
| 5,414,075 A | 5/1995 | Swan et al. |
| 5,466,233 A | 11/1995 | Weiner et al. |
| 5,512,329 A | 4/1996 | Guire et al. |
| 5,563,056 A | 10/1996 | Swan et al. |
| 5,609,629 A | 3/1997 | Fearnot et al. |
| 5,637,460 A | 6/1997 | Swan et al. |
| 5,677,007 A | 10/1997 | Tsai |
| 5,714,360 A | 2/1998 | Swan et al. |
| 5,756,145 A | 5/1998 | Darouiche |
| 5,783,502 A | 7/1998 | Swanson |
| 5,824,049 A | 10/1998 | Ragheb et al. |
| 5,837,313 A | 11/1998 | Ding et al. |
| 5,853,745 A | 12/1998 | Darouiche |
| 5,873,904 A | 2/1999 | Ragheb et al. |
| 5,916,153 A | 6/1999 | Rhea, Jr. |
| 5,984,878 A | 11/1999 | Engelson |
| 6,077,698 A | 6/2000 | Swan et al. |
| 6,090,995 A | 7/2000 | Reich et al. |
| 6,096,070 A | 8/2000 | Ragheb et al. |
| 6,099,562 A | 8/2000 | Ding et al. |
| 6,120,536 A | 9/2000 | Ding et al. |
| 6,214,901 B1 | 4/2001 | Chudzik et al. |
| 6,278,018 B1 | 8/2001 | Swan |
| 6,284,305 B1 | 9/2001 | Ding et al. |
| 6,299,604 B1 | 10/2001 | Ragheb et al. |
| 6,303,148 B1 | 10/2001 | Hennink et al. |
| 6,344,035 B1 | 2/2002 | Chudzik et al. |
| 6,358,556 B1 | 3/2002 | Ding et al. |
| 6,509,098 B1 | 1/2003 | Merrill et al. |
| 6,530,951 B1 | 3/2003 | Bates et al. |
| 6,558,315 B1 | 5/2003 | Kuyava |
| 6,562,136 B1 | 5/2003 | Chappa et al. |
| 6,603,040 B1 | 8/2003 | Swan |
| 6,616,982 B2 | 9/2003 | Merrill et al. |
| 6,620,194 B2 | 9/2003 | Ding et al. |
| 6,719,750 B2 | 4/2004 | Varner et al. |
| 6,730,064 B2 | 5/2004 | Ragheb et al. |
| 6,774,278 B1 | 8/2004 | Ragheb et al. |
| 6,924,390 B2 | 8/2005 | Swan |
| 7,077,910 B2 | 7/2006 | Chappa et al. |
| 2001/0007083 A1 | 7/2001 | Roorda |
| 2002/0004101 A1 | 1/2002 | Ding et al. |
| 2002/0032434 A1 | 3/2002 | Chudzik et al. |
| 2002/0032477 A1 | 3/2002 | Helmus et al. |
| 2002/0041899 A1 | 4/2002 | Chudzik et al. |
| 2002/0071902 A1 | 6/2002 | Ding et al. |
| 2002/0091433 A1 | 7/2002 | Ding et al. |

(Continued)

FOREIGN PATENT DOCUMENTS

WO    WO-03/105920    12/2003

(Continued)

OTHER PUBLICATIONS

Humphrey, Bruce et al., "Coatings: Using Parylene for Medical Substrate Coating", *Medical Plastics and Biomaterials Magazine* Jan. 1996, 1-3 (web).

Leventon, William et al., "Coatings: Coatings Cover Many Bases for Device Makers", *Medical Device & Diagnostic Industry* Jul. 2007, 1-3 (web).

Wolgemuth, Lonny et al., "Coatings: A Look at Parylene Coatings in Drug-Eluting Technologies", *Medical Device & Diagnostic Industry Magazine* Aug. 2005, 1-3 (web).

Wolgemuth, Lonny et al., "The Surface Modification Properties of Parylene for Medical Applications", *Medical Device Manufacturing & Technology* 2002, 1-4.

PCT International Search Report and Written Opinion from International Application No. PCT/US2007/079379, mailed Mar. 31, 2008, pp. 1-13.

(Continued)

*Primary Examiner* — Robert A Wax
*Assistant Examiner* — Danah Al-Awadi
(74) *Attorney, Agent, or Firm* — Pauly, Devries Smith & Deffner, L.L.C.

(57) ABSTRACT

Embodiments of the invention include multi-layered coatings for controlling the elution rates of active agents and methods. In an embodiment, the invention includes a method of applying an elution control coating to a substrate. The method can include depositing a coating solution onto the substrate to form a base layer. The method can also include selecting a desired concentration of the solvent based on a desired elution rate. The method can further include removing solvent from the base layer to reach a desired concentration of the solvent and depositing a layer of parylene on the base layer. In an embodiment, the invention can include a medical device including a substrate, a base layer, and a porous layer. The base layer can include a polymeric matrix and an active agent dispersed within the polymeric matrix. The porous layer can include parylene. Other embodiments are also included herein.

12 Claims, 4 Drawing Sheets

U.S. PATENT DOCUMENTS

| | | | |
|---|---|---|---|
| 2002/0188037 | A1 | 12/2002 | Chudzik et al. |
| 2003/0014036 | A1 | 1/2003 | Varner et al. |
| 2003/0028243 | A1 | 2/2003 | Bates et al. |
| 2003/0028244 | A1 | 2/2003 | Bates et al. |
| 2003/0036794 | A1 | 2/2003 | Ragheb et al. |
| 2003/0040790 | A1* | 2/2003 | Furst .................. 623/1.11 |
| 2003/0068355 | A1 | 4/2003 | Shanley et al. |
| 2003/0083646 | A1 | 5/2003 | Sirhan et al. |
| 2003/0087099 | A1 | 5/2003 | Merrill et al. |
| 2003/0129130 | A1 | 7/2003 | Guire et al. |
| 2003/0143315 | A1* | 7/2003 | Pui et al. .................. 427/2.1 |
| 2003/0204238 | A1 | 10/2003 | Tedeschi |
| 2004/0047909 | A1 | 3/2004 | Ragheb et al. |
| 2004/0062875 | A1 | 4/2004 | Chappa et al. |
| 2004/0133155 | A1 | 7/2004 | Verner et al. |
| 2004/0249443 | A1 | 12/2004 | Shanley et al. |
| 2004/0249445 | A1* | 12/2004 | Rosenthal et al. .......... 623/1.15 |
| 2005/0019371 | A1 | 1/2005 | Anderson et al. |
| 2005/0059956 | A1 | 3/2005 | Varner et al. |
| 2005/0158449 | A1 | 7/2005 | Chappa |
| 2005/0196424 | A1 | 9/2005 | Chappa |
| 2005/0255142 | A1 | 11/2005 | Chudzik et al. |
| 2005/0271703 | A1 | 12/2005 | Anderson et al. |
| 2005/0271706 | A1 | 12/2005 | Anderson et al. |
| 2005/0276837 | A1 | 12/2005 | Anderson et al. |
| 2005/0281858 | A1* | 12/2005 | Kloke et al. .................. 424/423 |
| 2005/0281863 | A1 | 12/2005 | Anderson et al. |
| 2005/0287188 | A1 | 12/2005 | Anderson et al. |
| 2006/0088653 | A1 | 4/2006 | Chappa |
| 2006/0110428 | A1 | 5/2006 | deJuan et al. |
| 2006/0134168 | A1 | 6/2006 | Chappa et al. |
| 2007/0026037 | A1 | 2/2007 | Kloke et al. |
| 2007/0065481 | A1 | 3/2007 | Chudzik et al. |
| 2007/0128343 | A1 | 6/2007 | Chappa |
| 2007/0218102 | A1 | 9/2007 | Chudzik et al. |
| 2007/0224247 | A1 | 9/2007 | Chudzik et al. |
| 2007/0260054 | A1 | 11/2007 | Chudzik |
| 2008/0020045 | A1 | 1/2008 | Chappa et al. |

FOREIGN PATENT DOCUMENTS

| | | |
|---|---|---|
| WO | WO-2004/014453 | 2/2004 |
| WO | WO-2007/016405 | 2/2007 |
| WO | WO-2007/109069 | 9/2007 |
| WO | WO-2008003043 | 1/2008 |
| WO | WO-2008022258 | 2/2008 |

OTHER PUBLICATIONS

PCT International Search Report and Written Opinion from International Application No. PCT/US2005/021834, mailed Jan. 12, 2005, pp. 1-13.

File History of U.S. Patent Application No. 11/156,245, Entitled "Devices, Articles, Coatings and Methods for Controlled Active Agent Release", (pp. 1-299).

* cited by examiner

MULTI-LAYERED COATINGS AND METHODS FOR CONTROLLING ELUTION OF ACTIVE AGENTS

This application is a continuation of U.S. application Ser. No. 11/860,856, filed on Sep. 25, 2007, which claims the benefit of U.S. provisional application Ser. No. 60/826,823, filed on Sep. 25, 2006, the contents of all of which are incorporated by reference herein.

FIELD OF THE INVENTION

The present invention relates to coatings and methods for controlling the elution of active agents. More specifically, the present invention relates to multi-layered coatings and methods for controlling the elution of active agents.

BACKGROUND OF THE INVENTION

Active agent elution control coatings are now commonly used to deliver active agents to tissues of the body. Elution control coatings can enable the delivery of an active agent over a period of time in order to optimize therapeutic effect. In addition, when disposed on a medical device, elution control coatings can enable site-specific active agent delivery because the medical device can be positioned as desired within the body of a patient.

A desirable elution rate for an active agent in one treatment scenario may be different than a desirable elution rate for an active agent in another treatment scenario. Therefore, it can be advantageous to be able to manipulate or change the elution kinetics of a coating in order to more closely match what is desirable for a specific treatment scenario.

Active agents delivered from elution control coatings can include many different types of compounds including small hydrophilic molecules, small hydrophobic molecules, macromolecules such as carbohydrates, peptides, proteins, and the like. Of these compounds, peptides and proteins can pose a challenge because, in general, they are susceptible to denaturation. In addition, the unique properties of peptides and proteins, such as their relatively large size, can frequently result in them being delivered either more quickly or more slowly than desired.

Accordingly, there is a need for coatings that can deliver active agents at desirable rates and methods of making the same. There is also a need for coatings that can be used to control the elution rate of macromolecules such as peptides and proteins.

SUMMARY OF THE INVENTION

Embodiments of the invention include multi-layered coatings for controlling the elution rates of active agents and methods of making the same. In an embodiment, the invention includes a method of applying an elution control coating to a substrate. The method can include depositing a coating solution onto the substrate to form a base layer, the coating solution including an active agent, a polymer, and a solvent. The method can also include selecting a desired concentration of the solvent based on a desired elution rate. The method can further include removing solvent from the base layer to reach a desired concentration of the solvent and depositing a layer of parylene on the base layer.

In an embodiment, the invention can include a method of depositing a multi-layer elution control coating onto a substrate. The method can include depositing a coating solution onto the substrate to form a base layer, the coating solution including an active agent, a polymer, and a solvent. The method can also include storing the substrate and base layer under vacuum for a period of time greater than about 30 minutes to form a degassed base layer and depositing a layer of parylene on the degassed base layer.

In an embodiment, the invention can include a medical device including a substrate, a base layer, and a porous layer. The base layer can be disposed on the substrate. The base layer can include a polymeric matrix and an active agent. The active agent can be dispersed within the polymeric matrix. The active agent can be selected from the group consisting of peptides, proteins, antibodies, and antibody derivatives. The porous layer can be disposed on the base layer. The porous layer can include parylene.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

Figure 1:
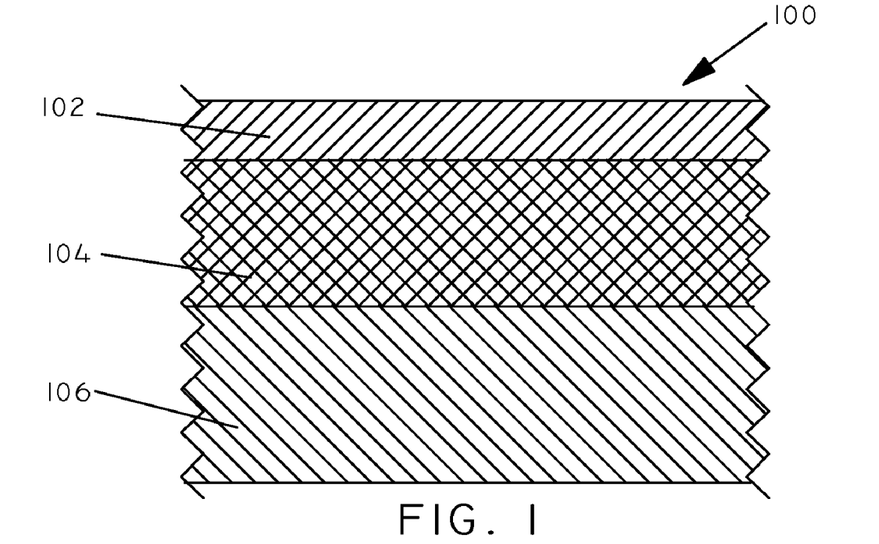
FIG. 1 is a cross-sectional view of a multi-layered coating system in accordance with an embodiment of the invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As described above, a desirable elution rate for an active agent in one treatment scenario may be different than a desirable elution rate for an active agent in another treatment scenario. Therefore, it can be advantageous to be able to manipulate or change the elution rate of a coating to optimize treatment.

Elution of some active agents, such as peptides and proteins, from coatings can pose a particular challenge. The activity of peptides and proteins is typically dependent on their three-dimensional structure which can be disrupted by heat, solvents, changing ionic concentrations, shearing forces, etc. Therefore, such active agents need to be handled carefully to preserve their activity. In addition, the size of peptides and proteins can make it difficult to elute them from a coating at a desirable rate. Frequently, elution control coatings elute such active agents either too quickly or too slowly.

The polymer known as parylene usually forms a continuous barrier to the passage of molecules. Because of its barrier properties, parylene has found many industrial uses including as a protective coating on electronic equipment. However, as shown herein, a multilayered coating including a top coat of parylene can be manipulated so that it provides a desirable elution rate of an active agent such as a peptide or protein. While not intending to be bound by theory, it is believed that if a parylene layer is applied while a component, such as a solvent, is out-gassing from the underlying surface, the resulting parylene layer becomes porous and can be used to control the elution of active agents such as peptides and proteins. As shown in example 2 below, the elution rate of a coating can be manipulated by controlling the amount of a vaporizable component, such as a solvent, in the coating layer before a layer of parylene is applied, such as by drying under vacuum, degassing, or another like technique for removing the vaporizable component.

In an embodiment, the invention includes a method of applying an elution control coating to a substrate including depositing a coating solution onto the substrate to form a base layer, the coating solution comprising an active agent, a polymer, and a solvent; selecting a desired concentration of the solvent based on a desired elution rate; removing solvent from the base layer to reach the desired concentration of the solvent; and depositing a top layer on the base layer, the top layer comprising parylene.

Some polymers used to make elution control matrices are relatively hydrophobic. Hydrophobic polymers can have various properties that are conducive to creating elution control coatings with desirable release properties. However, some active agents, such as peptides and proteins, may elute from a hydrophobic polymer matrix more quickly than desired for certain applications. Deposition of a parylene layer over a hydrophobic polymer matrix can serve to slow down the elution rate of an active agent. Exemplary hydrophobic polymers are described more fully below.

In an embodiment, the invention includes a medical device including a substrate; a base layer disposed on the substrate, the base layer comprising a hydrophobic polymeric matrix and an active agent, the active agent dispersed within the hydrophobic polymeric matrix, the active agent comprising a macromolecule; and a top layer disposed directly on the base layer, the top layer comprising parylene and having a thickness of between about 0.01 microns and about 5 microns.

Elution control matrices including both degradable and non-degradable polymers can offer various advantages. By way of example, combination degradable/non-degradable matrices can have structural integrity sufficient to prevent portions of the coating from breaking off or otherwise separating under the conditions of use. Combination degradable/non-degradable matrices of the invention can also advantageously preserve activity of an active agent eluted from the combination degradable/non-degradable matrix. Deposition of a parylene layer over a combination degradable/non-degradable matrix can serve to further increase the structural integrity of the resulting coating. Further, deposition of a parylene layer over a combination degradable/non-degradable matrix can provide an additional means of controlling the elution rate of an active agent eluted from the coating.

In an embodiment, the invention includes a medical device including a substrate; a base layer disposed on the substrate, the base layer comprising a polymeric matrix and an active agent, the polymer matrix including a degradable polymer and a non-degradable polymer, the active agent dispersed within the polymeric matrix, the active agent comprising a macromolecule; and a top layer disposed on the active agent layer, the top layer comprising parylene and having a thickness of between about 0.01 microns and about 5 microns.

Referring now to FIG. 1, a cross-sectional view of a multilayer elution control coating 100 is shown in accordance with an embodiment of the invention. A base layer 104 is disposed on a substrate 106. The substrate 106 can include various components as described more fully below. The base layer 104 may include one or more degradable polymers, one or more non-degradable polymers, or combinations of both. In some embodiments, the base layer 104 includes a degradable polymer interspersed with a non-degradable polymer. In some embodiments the base layer 104 includes a hydrophobic polymer. One or more base layers can be included. In some embodiments, multi-layer elution control coatings can include a first base layer and a second base layer, the second either the same or different than the first. In some cases, a different material is disposed between the base layer 104 and the substrate 106. Exemplary degradable and non-degradable polymers are described in more detail below.

The base layer 104 can also include one or more active agents. In some embodiments, an active agent is dispersed within the base layer 104. As used herein, the term "dispersed" shall refer to the property of being distributed in a soluble or insoluble state. As used herein, the term "active agent" means a compound that has a particular desired activity. For example, an active agent can be a therapeutic compound that exerts a specific activity on a subject. Exemplary active agents can include peptides, proteins, carbohydrates, nucleic acids, lipids, polysaccharides, synthetic inorganic or organic molecules, or combinations thereof that cause a desired biological effect when administered to an animal, including but not limited to birds and mammals, including humans.

Active agents used with the invention can specifically include proteins, protein fragments, peptides, polypeptides, and the like. Peptides can include any compound containing two or more amino-acid residues joined by amide bonds formed from the carboxyl group of one amino acid and the amino group of the next one. By way of example, peptides can include glycosylated proteins, antibodies (both monoclonal and polyclonal), antibody derivatives (including diabodies, f(ab) fragments, humanized antibodies, etc.), cytokines, growth factors, receptor ligands, enzymes, and the like. In some embodiments, the active agent is selected from the group consisting of peptides and proteins. In some embodiments, the active agent is a macromolecule. Macromolecules can include molecules having a molecular weight of greater than about 10 kDa. The base layer 104 can be configured to control the rate at which the active agent is eluted there from.

The base layer 104 can also include one or more solvents. Solvents can be used to aid in the process of depositing one or more polymers and one or more active agents in the base layer. Solvents can include both polar and non-polar solvents.

Solvents can include components that are vaporizable. As used herein, the term "vaporizable" shall refer to components having the property of forming a vapor or gas under conditions that can include ambient or elevated temperatures and atmospheric or vacuum pressures. In some embodiments, the base layer 104 can include one or more volatile components. Solvents can include water, alcohols (e.g., methanol, butanol, propanol, and isopropanol (isopropyl alcohol)), alkanes (e.g., halogenated or unhalogenated alkanes such as chloroform, hexane, and cyclohexane), amides (e.g., dimethylformamide), ethers (e.g., THF and dioxolane), ketones (e.g., methylethylketone), aromatic compounds (e.g., toluene and xylene), nitriles (e.g., acetonitrile) and esters (e.g., ethyl acetate). In some embodiments, one or more polymers of the base layer 104 are soluble in the solvent. In some embodiments, one or more active agents of the base layer 104 are soluble in the solvent. The solvent can be non-polymeric.

The base layer 104 can be deposited onto the substrate 106 using any of a variety of coating techniques including dip-coating, spray-coating (including both gas-atomization and ultrasonic atomization), fogging, brush coating, press coating, blade coating, and the like. The base layer 104 may be applied as a coating solution and may be applied under conditions where atmospheric characteristics such as relative humidity, temperature, gaseous composition, and the like are controlled. In some embodiments, the coating solution is applied using a spray technique. Exemplary spray coating equipment that can be used to apply components of the invention can be found in U.S. Pat. No. 6,562,136; U.S. Pat. No. 7,077,910; U.S. Pub. App. No. US 2004/0062875; U.S. Pub. App. No. 2005/0158449; U.S. Pub. App. No. 2006/0088653; U.S. Pub. App. No. 2005/0196424; and U.S. Pub. App. No. 2007/0128343, the contents of which are all hereby incorporated by reference.

The thickness of the base layer 104 can depend on many factors including, for example, the specific polymers used in the matrix, the desired loading of active agent within the base layer 104, the type of medical device being coated, etc. In some embodiments, the base layer 104 is from about 0.5 microns to about 500 microns thick.

A top layer 102 is disposed on the base layer 104. In some embodiments, the top layer 102 is disposed directly upon the base layer 104. In other embodiments, a different material or layer is disposed between the top layer 102 and the base layer 104. The top layer 102 can comprise parylene. The term "parylene" as used herein shall refer to a polymer belonging to the group of polymers based on p-xylene (substituted or unsubstituted). Parylenes have the repeating structure -(p-$CH_2$—$C_6H_4$—$CH_2$)$_n$—. Common parylene polymers include poly(2-chloro-paraxylylene) ("parylene C"), poly(paraxylylene) ("parylene N"), and poly(2,5-dichloro-paraxylylene) ("parylene D"). In a particular embodiment, the top layer 102 includes poly(2-chloro-paraxylylene) ("parylene C"). The top layer 102 can also include mono-, di-, tri-, and tetra-halo substituted polyparaxylylenes. In an embodiment, the top layer 102 includes mono-, di-, tri-, or tetra-chloro substituted polyparaxylylene. In an embodiment, the top layer 102 includes mono-, di-, tri-, or tetra-fluoro substituted polyparaxylylene. Other parylene derivatives can used including poly(dimethoxy-p-xylylene), poly(sulfo-p-xylylene), poly(iodo-p-xylylene), poly(trifluoro-p-xylylene), poly(difluoro-p-xylylene), and poly(fluoro-p-xylylene).

Deposition of the top layer 102 can be performed using various techniques. In an embodiment, the top layer 102 can be deposited using a vacuum vapor deposition system. In some vacuum vapor deposition systems a polymer charge is vaporized in a vaporization chamber and then passes through a cracking chamber where parylene dimer vapor is cracked into activated monomer vapor. Vaporized activated monomer is then usually deposited onto a substrate in a deposition chamber. An exemplary vacuum deposition system is the PDS-2010 LABCOTER® available from Specialty Coating Systems (Indianapolis, Ind.).

As shown in the examples below, the condition of the base layer 104 while the top layer 102 is being deposited can affect the resulting elution rate of the multi-layer elution control coating. While not intending to be bound by theory, if the top layer 102 is applied while a component, such as a solvent, is out-gassing or evaporating from the base layer 104, the parylene layer can be made porous. As such, the elution rate of an active agent from the multi-layer elution control coating 100 can be decreased by decreasing the amount of vaporizable components therein prior to depositing the top layer 102 onto the base layer 104. Conversely, the elution rate of an active agent from the multi-layer elution control coating 100 can be increased by increasing the amount of vaporizable components therein prior to depositing the top layer 102 onto the base layer 104.

The concentration of vaporizable components in the base layer 104 can be increased or decreased in various ways. In some embodiments, a smaller amount of vaporizable components are added to a coating solution that is used to form the base layer 104. In other embodiments, vaporizable components are removed from the base layer 104 after it is first applied to a substrate. It will be appreciated that vaporizable components can be removed from the base layer 104 in various ways. For example, the base layer 104, as deposited onto a substrate, can simply be stored at ambient temperature for a period of time. Alternatively, the base layer 104 can be held at an elevated temperature for a period of time. However, elevated temperatures can contribute to degradation or denaturation of peptides and proteins. Another method of removing vaporizable components from the base layer 104 can include storing it under vacuum conditions for a period of time. In some embodiments, a base layer 104 disposed on a substrate is stored under vacuum for a period of time greater than about 30 minutes. In some embodiments, a base layer 104 disposed on a substrate is stored under vacuum for a period of time greater than about one hour. In some embodiments, a base layer 104 disposed on a substrate is stored under vacuum for a period of time greater than about twelve hours. In some embodiments, a base layer 104 disposed on a substrate is stored under vacuum for a period of time greater than about one day. In some embodiments, a base layer 104 disposed on a substrate is stored under vacuum for a period of time greater than about one week.

In addition to other aspects, the thickness of the top layer 102 can impact the elution rate of an active agent passing the top layer 102. In general, the thicker the top layer 102 is, the slower the resulting elution rate will be. In some embodiments, the top layer 102 is from about 0.01 microns to about 5.0 microns thick.

In some embodiments, the base layer 104 is not disposed on a substrate. By way of example, the base layer 104 can form a bead or a film and the top layer 102 can be disposed over the base layer 104.

Figure 2:
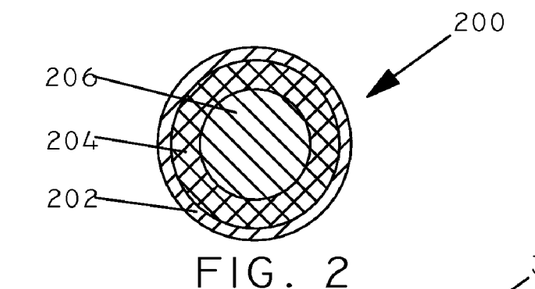
FIG. 2 is a cross-sectional view of a multi-layered coating system in accordance with another embodiment of the invention.

FIG. 2 shows a cross-sectional view of a multi-layer elution control coating disposed on a substrate in accordance with another embodiment of the invention. A base layer 204 is disposed on a substrate 206. The base layer 204 can include one or more polymers and/or one or more active agents. The base layer 204 can surround the substrate 206. A top layer 202 is disposed on the base layer 204. The top layer 202 can include parylene. The top layer 202 can completely cover the base layer 204.

Figure 3:
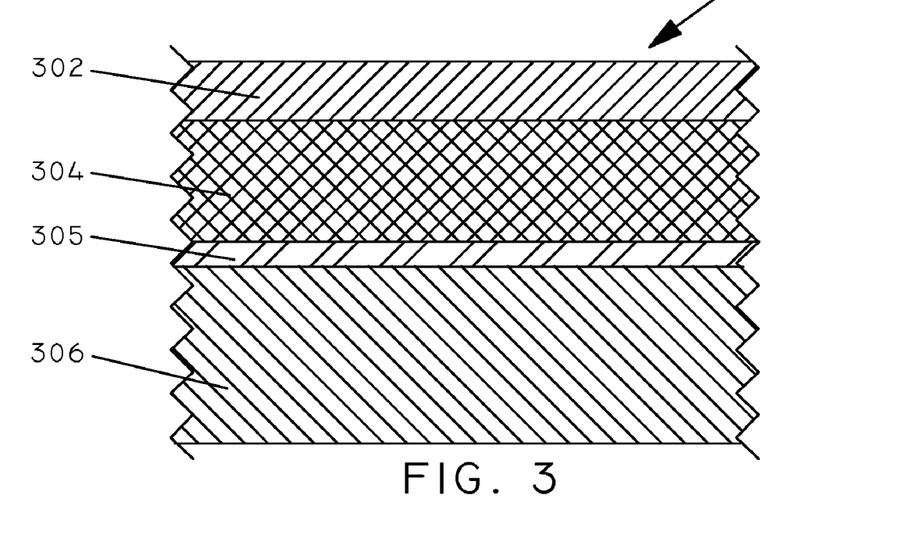
FIG. 3 is a cross-sectional view of a multi-layered coating system in accordance with another embodiment of the invention.

FIG. 3 shows a cross-sectional view of a multi-layer elution control coating disposed on a substrate in accordance with another embodiment of the invention. An underlying layer 305 is disposed on a substrate 306. The underlying layer 305 can include one or more polymers. The underlying layer 305 can also include one or more active agents. In some embodiments, the underlying layer 305 can be configured to elute an active agent. In some embodiments, the underlying layer 305 includes parylene. In some embodiments, the underlying layer 305 can improve adhesion of the other layers to the substrate 306. A base layer 304 is disposed on the underlying layer 305. The base layer 304 can include one or more polymers and/or one or more active agents. A top layer 302 is disposed on the base layer 304. The top layer 302 can include parylene.

Substrates

It will be appreciated that embodiments of the invention can be used in conjunction with various types of substrates. Exemplary substrates can include metals, polymers, ceramics, and natural materials. Metals can include, but are not limited to, cobalt, chromium, nickel, titanium, tantalum, iridium, tungsten and alloys such as stainless steel, nitinol or cobalt chromium. Suitable metals can also include the noble metals such as gold, silver, copper, platinum, and alloys including the same.

Substrate polymers include those formed of synthetic polymers, including oligomers, homopolymers, and copolymers resulting from either addition or condensation polymerizations. Examples include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, styrene, vinyl chloride, vinyl acetate, vinyl pyrrolidone, and vinylidene difluoride, condensation polymers including, but are not limited to, polyamides such as polycaprolactam, polylauryl lactam, polyhexamethylene adipamide, and polyhexamethylene dodecanediamide, and also polyurethanes, polycarbonates, polysulfones, poly(ethylene terephthalate), polytetrafluoroethylene, polyethylene, polypropylene, polylactic acid, polyglycolic acid, polysiloxanes (silicones), cellulose, and polyetheretherketone.

Embodiments of the invention can also include the use of ceramics as a substrate. Ceramics include, but are not limited to, silicon nitride, silicon carbide, zirconia, and alumina, as well as glass, silica, and sapphire.

Certain natural materials can also be used in some embodiments including human tissue, when used as a component of a device, such as bone, cartilage, skin and enamel; and other organic materials such as wood, cellulose, compressed carbon, rubber, silk, wool, and cotton. Substrates can also include carbon fiber. Substrates can also include resins, polysaccharides, silicon, or silica-based materials, glass, films, gels, and membranes.

Medical Devices

Figure 4:
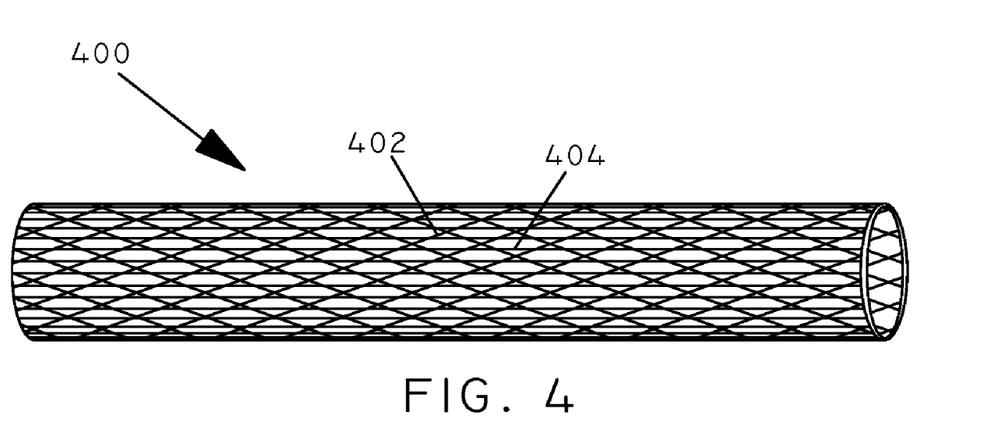
FIG. 4 is a perspective view of a stent coated with a multi-layered coating system in accordance with an embodiment of the invention.
Figure 5:
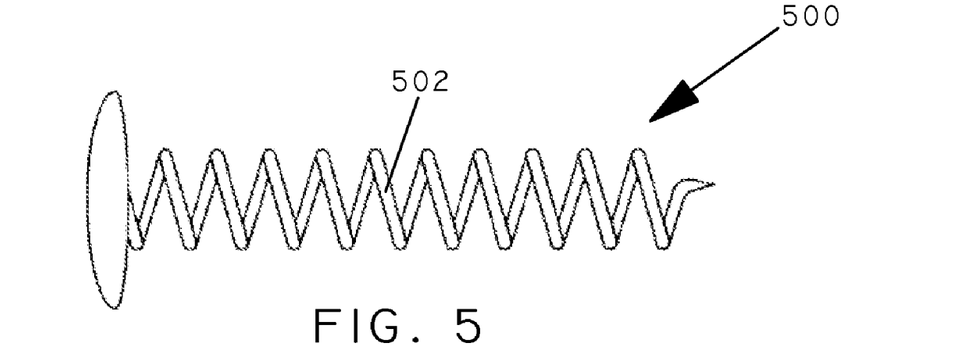
FIG. 5 is a perspective view of a coil coated with a multi-layered coating system in accordance with an embodiment of the invention.

It will be appreciated that embodiments of the invention can be used in conjunction with, and can include, many different types of medical devices. For example, in FIG. 4 a perspective view of a stent 400 is shown in accordance with an embodiment of the invention. The stent 400 is fabricated with a mesh-type construction and includes a plurality of wires or struts 402 that can be made of various materials including metals and polymers. A multi-layer elution control coating including a base layer and a top layer can be deposited on the wires or struts 402. In FIG. 5, a perspective view of a coil 500 is shown in accordance with an embodiment of the invention. The coil 500 includes a curved wire 502 that can be made of various materials including metals and polymers. A multi-layer elution control coating including a base layer and a top layer can be deposited on the coil 500. Specifically, a multi-layer elution control coating can be deposited on the curved wire 502.

Embodiments of the invention can include and can be used with both implantable devices and non-implantable medical devices. Embodiments of the invention can include and can be used with implantable, or transitorily implantable, devices including, but not limited to, vascular devices such as grafts (e.g., abdominal aortic aneurysm grafts, etc.), stents (e.g., self-expanding stents typically made from nitinol, balloon-expanded stents typically prepared from stainless steel, degradable coronary stents, etc.), catheters (including arterial, intravenous, blood pressure, stent graft, etc.), valves (e.g., polymeric or carbon mechanical valves, tissue valves, valve designs including percutaneous, sewing cuff, and the like), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies (e.g., batteries, etc.), peripheral cardiovascular devices, atrial septal defect closures, left atrial appendage filters, valve annuloplasty devices (e.g., annuloplasty rings), mitral valve repair devices, vascular intervention devices, ventricular assist pumps, and vascular access devices (including parenteral feeding catheters, vascular access ports, central venous access catheters); surgical devices such as sutures of all types, staples, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices including orbital implants, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches; ear nose and throat devices such as nasal buttons, nasal and airway splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; biosensor devices including glucose sensors, cardiac sensors, intra-arterial blood gas sensors; oncological implants; and pain management implants.

Classes of non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

In some aspects, embodiments of the invention can include and be utilized in conjunction with ophthalmic devices. Suitable ophthalmic devices in accordance with these aspects can provide bioactive agent to any desired area of the eye. In some aspects, the devices can be utilized to deliver bioactive agent to an anterior segment of the eye (in front of the lens), and/or a posterior segment of the eye (behind the lens). Suitable ophthalmic devices can also be utilized to provide bioactive agent to tissues in proximity to the eye, when desired.

In some aspects, embodiments of the invention can be utilized in conjunction with ophthalmic devices configured for placement at an external or internal site of the eye. Suitable external devices can be configured for topical administration of bioactive agent. Such external devices can reside on an external surface of the eye, such as the cornea (for example, contact lenses) or bulbar conjunctiva. In some embodiments, suitable external devices can reside in proximity to an external surface of the eye.

Devices configured for placement at an internal site of the eye can reside within any desired area of the eye. In some aspects, the ophthalmic devices can be configured for placement at an intraocular site, such as the vitreous. Illustrative intraocular devices include, but are not limited to, those described in U.S. Pat. Nos. 6,719,750 B2 ("Devices for Intraocular Drug Delivery," Varner et al.) and 5,466,233 ("Tack for Intraocular Drug Delivery and Method for Inserting and Removing Same," Weiner et al.); U.S. Publication Nos. 2005/0019371 A1 ("Controlled Release Bioactive Agent Delivery Device," Anderson et al.), 2004/0133155 A1 ("Devices for Intraocular Drug Delivery," Varner et al.), 2005/0059956 A1 ("Devices for Intraocular Drug Delivery," Varner et al.), and 2003/0014036 A1 ("Reservoir Device for Intraocular Drug Delivery," Varner et al.); and U.S. application Ser. Nos. 11/204,195 (filed Aug. 15, 2005, Anderson et al.), 11/204,271 (filed Aug. 15, 2005, Anderson et al.), 11/203,981 (filed Aug. 15, 2005, Anderson et al.), 11/203,879 (filed Aug. 15, 2005, Anderson et al.), 11/203,931 (filed Aug. 15, 2005, Anderson et al.); and related applications.

In some aspects, the ophthalmic devices can be configured for placement at a subretinal area within the eye. Illustrative ophthalmic devices for subretinal application include, but are not limited to, those described in U.S. Patent Publication No. 2005/0143363 ("Method for Subretinal Administration of Therapeutics Including Steroids; Method for Localizing Pharmacodynamic Action at the Choroid and the Retina; and Related Methods for Treatment and/or Prevention of Retinal Diseases," de Juan et al.); U.S. application Ser. No. 11/175,850 ("Methods and Devices for the Treatment of Ocular Conditions," de Juan et al.); and related applications.

Suitable ophthalmic devices can be configured for placement within any desired tissues of the eye. For example, ophthalmic devices can be configured for placement at a subconjunctival area of the eye, such as devices positioned extrasclerally but under the conjunctiva, such as glaucoma drainage devices and the like.

Hydrophobic Polymers

In an embodiment, the base layer can include a hydrophobic polymer. One method of defining the hydrophobicity of a polymer is by the solubility parameter (or Hildebrand parameter) of the polymer. The solubility parameter describes the attractive strength between molecules of the material. The solubility parameter is represented by Equation 1:

$$\delta = (\Delta E^v / V)^{1/2} \qquad \text{(Equation 1)}$$

where $\delta$=solubility parameter $((cal/cm^3)^{1/2})$
$\Delta E^v$=energy of vaporization (cal)
V=molar volume $(cm^3)$ Solubility parameters cannot be calculated for polymers from heat of vaporization data because of their nonvolatility. Accordingly, solubility parameters must be calculated indirectly. One method involves identifying solvents in which a polymer dissolves without a change in heat or volume and then defining the solubility parameter of the polymer to be the same as the solubility parameters of the identified solvents. A more complete discussion of solubility parameters and methods of calculating the same can be found in Brandup et al., Polymer Handbook, 4th Ed., John Wiley & Sons, N.Y. (1999) beginning at VII p. 675.

As a general rule, the value of the solubility parameter $\delta$ is inversely proportional to the degree of hydrophobicity of a polymer. Thus, polymers that are very hydrophobic may have a low solubility parameter value. This general proposition is particularly applicable for polymers having a glass transition temperature below physiological temperature. In an embodiment, hydrophobic polymers used with the invention have a solubility parameter less than about 11.0 $(cal/cm^3)^{1/2}$. In an embodiment, hydrophobic polymers used with the invention have a solubility parameter of less than about 10.0 $(cal/cm^3)^{1/2}$.

Degradable Polymers

In an embodiment, the base layer can include one or more degradable polymers. The term "degradable" as used herein with reference to polymers, shall refer to those natural or synthetic polymers that break down under physiological conditions into constituent components over a period of time. By way of example, many degradable polymers include hydrolytically unstable linkages in the polymeric backbone. The cleavage of these unstable linkages leads to degradation of the polymer. The terms "erodible", "bioerodible", "biodegradable" and "non-durable" shall be used herein interchangeably with the term "degradable". Degradable polymers can include both natural or synthetic polymers. Examples of degradable polymers can include those with hydrolytically unstable linkages in the polymeric backbone. Degradable polymers of the invention can include both those with bulk erosion characteristics and those with surface erosion characteristics.

Synthetic degradable polymers can include: degradable polyesters (such as poly(glycolic acid), poly(lactic acid), poly(lactic-co-glycolic acid), poly(dioxanone), polylactones (e.g., poly(caprolactone)), poly(3-hydroxybutyrate), poly(3-hydroxyvalerate), poly(valerolactone), poly(tartronic acid), poly(B-malonic acid), poly(propylene fumarate)); degradable polyesteramides; degradable polyanhydrides (such as poly(sebacic acid), poly(1,6-bis(carboxyphenoxy)hexane, poly(1,3-bis(carboxyphenoxy)propane); degradable polycarbonates (such as tyrosine-based polycarbonates); degradable polyiminocarbonates; degradable polyarylates (such as tyrosine-based polyarylates); degradable polyorthoesters; degradable polyurethanes; degradable polyphosphazenes; and degradable polyhydroxyalkanoates; and copolymers thereof.

Natural or naturally-based degradable polymers can include polysaccharides and modified polysaccharides such as starch, cellulose, chitin, chitosan, and copolymers thereof.

Specific examples of degradable polymers include poly (ether ester) multiblock copolymers based on poly(ethylene glycol) (PEG) and poly(butylene terephthalate) that can be described by the following general structure:

where —$C_6H_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. n can be selected such that the molecular weight of the PEG block is between about 300 and about 4000. X and y can be selected so that the multiblock copolymer contains from about 55% up to about 80% PEG by weight. The block copolymer can be engineered to provide a wide array of physical characteristics (e.g., hydrophilicity, adherence, strength, malleability, degradability, durability, flexibility) and active agent release characteristics (e.g., through controlled polymer degradation and swelling) by varying the values of n, x and y in the copolymer structure.

Degradable polyesteramides can include those formed from the monomers OH-x-OH, z, and COOH-y-COOH, wherein x is alkyl, y is alkyl, and z is leucine or phenylalanine.

Degradable polymeric materials can also be selected from: (a) non-peptide polyamino polymers; (b) polyiminocarbonates; (c) amino acid-derived polycarbonates and polyarylates; and (d) poly(alkylene oxide) polymers.

In an embodiment, the degradable polymeric material is composed of a non-peptide polyamino acid polymer. Exemplary non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, including two or three amino acid units having one of the following two structures illustrated below:

wherein the monomer units are joined via hydrolytically labile bonds at not less than one of the side groups $R_1$, $R_2$, and $R_3$, and where $R_1$, $R_2$, $R_3$ are the side chains of naturally occurring amino acids; Z is any desirable amine protecting group or hydrogen; and Y is any desirable carboxyl protecting group or hydroxyl. Each monomer unit comprises naturally occurring amino acids that are then polymerized as monomer units via linkages other than by the amide or "peptide" bond. The monomer units can be composed of two or three amino acids united through a peptide bond and thus comprise dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are non-toxic, are degradable, and can provide zero-order release kinetics for the delivery of active agents in a variety of therapeutic applications. According to these aspects, the amino acids are selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, ornithine, lanthionine, hypoglycin A, β-alanine, γ-amino butyric acid, a aminoadipic acid, canavanine, venkolic acid, thiolhistidine, ergothionine, dihydroxyphenylalanine, and other amino acids well recognized and characterized in protein chemistry. Degradable polymers of the invention can also include polymerized polysaccharides such as those described in U.S. Publ. Pat. Application No. 2005/0255142, entitled "COATINGS FOR MEDICAL ARTICLES INCLUDING NATURAL BIODEGRADABLE POLYSACCHARIDES", U.S. Publ. Pat. Application No. 2007/0065481, entitled "COATINGS INCLUDING NATURAL BIODEGRADABLE POLYSACCHARIDES AND USES THEREOF", and in U.S. Application No. 60/782,957, entitled "HYDROPHOBIC DERIVATIVES OF NATURAL BIODEGRADABLE POLYSACCHARIDES", all of which are herein incorporated by reference.

Degradable polymers of the invention can also include dextran based polymers such as those described in U.S. Pat. No. 6,303,148, entitled "PROCESS FOR THE PREPARATION OF A CONTROLLED RELEASE SYTEM". Exemplary dextran based degradable polymers including those available commercially under the trade name OCTODEX.

Degradable polymers of the invention can further include collagen/hyaluronic acid polymers.

Degradable polymers of the invention can include multi-block copolymers, comprising at least two hydrolysable segments derived from pre-polymers A and B, which segments are linked by a multi-functional chain-extender and are chosen from the pre-polymers A and B, and triblock copolymers ABA and BAB, wherein the multi-block copolymer is amorphous and has one or more glass transition temperatures (Tg) of at most 37° C. (Tg) at physiological (body) conditions. The pre-polymers A and B can be a hydrolysable polyester, polyetherester, polycarbonate, polyestercarbonate, polyanhydride or copolymers thereof, derived from cyclic monomers such as lactide (L,D or L/D), glycolide, ϵ-caprolactone, δ-valerolactone, trimethylene carbonate, tetramethylene carbonate, 1,5-dioxepane-2-one, 1,4-dioxane-2-one (para-dioxanone) or cyclic anhydrides (oxepane-2,7-dione). The composition of the pre-polymers can be chosen in such a way that the maximum glass transition temperature of the resulting copolymer is below 37° C. at body conditions. To fulfill the requirement of a Tg below 37° C., some of the above-mentioned monomers or combinations of monomers can be more preferred than others. This may by itself lower the Tg, or the pre-polymer is initiated with a polyethylene glycol with sufficient molecular weight to lower the glass transition temperature of the copolymer. The degradable multi-block copolymers can include hydrolysable sequences being amorphous and the segments can be linked by a multifunctional chain-extender, the segments having different physical and degradation characteristics. For example, a multi-block co-polyester consisting of a glycolide-ε-caprolactone segment and a lactide-glycolide segment can be composed of two different polyester pre-polymers. By controlling the segment monomer composition, segment ratio and length, a variety of polymers with properties that can easily be tuned can be obtained.

Non-Degradable Polymers

Embodiments of the invention can include one or more non-degradable (durable) polymers in the base layer. In an embodiment, the non-degradable polymer includes a plurality of polymers, including a first polymer and a second polymer. When the coating solution contains only one polymer, it can be either a first or second polymer as described herein. As used herein, term "(meth)acrylate" when used in describing polymers shall mean the form including the methyl group (methacrylate) or the form without the methyl group (acrylate).

First polymers of the invention can include a polymer selected from the group consisting of poly(alkyl(meth)acrylates) and poly(aromatic(meth)acrylates), where "(meth)" will be understood by those skilled in the art to include such molecules in either the acrylic and/or methacrylic form (corresponding to the acrylates and/or methacrylates, respectively). An exemplary first polymer is poly(n-butyl methacrylate) (pBMA). Such polymers are available commercially, e.g., from Aldrich, with molecular weights ranging from about 200,000 Daltons to about 320,000 Daltons, and with varying inherent viscosity, solubility, and form (e.g., as crystals or powder). In some embodiments, poly(n-butyl methacrylate) (pBMA) is used with a molecular weight of about 200,000 Daltons to about 300,000 Daltons.

Examples of suitable first polymers also include polymers selected from the group consisting of poly(aryl(meth)acrylates), poly(aralkyl (meth)acrylates), and poly(aryloxyalkyl (meth)acrylates). Such terms are used to describe polymeric structures wherein at least one carbon chain and at least one aromatic ring are combined with acrylic groups, typically esters, to provide a composition. In particular, exemplary polymeric structures include those with aryl groups having from 6 to 16 carbon atoms and with weight average molecular weights from about 50 to about 900 kilodaltons. Suitable poly(aralkyl(meth)acrylates), poly(arylalky(meth)acrylates) or poly(aryloxyalkyl (meth)acrylates) can be made from aromatic esters derived from alcohols also containing aromatic moieties.

Examples of poly(aryl(meth)acrylates) include poly(9-anthracenyl methacrylate), poly(chlorophenylacrylate), poly (methacryloxy-2-hydroxybenzophenone), poly(methacryloxybenzotriazole), poly(naphthylacrylate) and -methacrylate), poly(4-nitrophenyl acrylate), poly(pentachloro(bromo, fluoro) acrylate) and -methacrylate), and poly(phenyl acrylate) and -methacrylate. Examples of poly (aralkyl (meth)acrylates) include poly(benzyl acrylate) and -methacrylate), poly(2-phenethyl acrylate) and -methacrylate, and poly(1-pyrenylmethyl methacrylate). Examples of poly(aryloxyalkyl (meth)acrylates) include poly(phenoxyethyl acrylate) and -methacrylate), and poly(polyethylene glycol phenyl ether acrylates) and -methacrylates with varying polyethylene glycol molecular weights.

Examples of suitable second polymers are available commercially and include poly(ethylene-co-vinyl acetate) (pEVA) having vinyl acetate concentrations of between about 10% and about 50% (12%, 14%, 18%, 25%, 33% versions are commercially available), in the form of beads, pellets, granules, etc. pEVA co-polymers with lower percent vinyl acetate become increasingly insoluble in typical solvents, whereas those with higher percent vinyl acetate become decreasingly durable.

An exemplary polymer mixture includes mixtures of pBMA and pEVA. This mixture of polymers can be used with absolute polymer concentrations (i.e., the total combined concentrations of both polymers in the coating material), of between about 0.25 wt. % and about 99 wt. %. This mixture can also be used with individual polymer concentrations in the coating solution of between about 0.05 wt. % and about 99 wt. %. In one embodiment the polymer mixture includes pBMA with a molecular weight of from 100 kilodaltons to 900 kilodaltons and a pEVA copolymer with a vinyl acetate content of from 24 to 36 weight percent. In an embodiment the polymer mixture includes pBMA with a molecular weight of from 200 kilodaltons to 300 kilodaltons and a pEVA copolymer with a vinyl acetate content of from 24 to 36 weight percent. The concentration of the active agent or agents dissolved or suspended in the coating mixture can range from 0.01 to 99 percent, by weight, based on the weight of the final coating material.

Second polymers can also comprise one or more polymers selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers.

Poly(alkylene-co-alkyl(meth)acrylates) include those copolymers in which the alkyl groups are either linear or branched, and substituted or unsubstituted with non-interfering groups or atoms. Such alkyl groups can comprise from 1 to 8 carbon atoms, inclusive. Such alkyl groups can comprise from 1 to 4 carbon atoms, inclusive. In an embodiment, the alkyl group is methyl. In some embodiments, copolymers that include such alkyl groups can comprise from about 15% to about 80% (wt) of alkyl acrylate. When the alkyl group is methyl, the polymer contains from about 20% to about 40% methyl acrylate in some embodiments, and from about 25% to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Alternatively, second polymers can comprise ethylene copolymers with other alkylenes, which in turn, can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), polyethylene-co-1-butene-co-1-hexene) and/or poly(ethylene-co-1-octene).

"Polybutenes" include polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative second polymers include diolefin-derived, non-aromatic polymers and copolymers, including those in which the diolefin monomer used to prepare the polymer or copolymer is selected from butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl (meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a molecular weight between about 150 kilodaltons and about 1,000 kilodaltons. In an embodiment, polymers and copolymers have a molecular weight between about 200 kilodaltons and about 600 kilodaltons.

Additional alternative second polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl (meth)acrylate (e.g., methyl methacrylate) and/or butene. Useful block copolymers include copolymer containing (a) blocks of polystyrene, (b) blocks of an polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt.) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative second polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have a molecular weight from about 100 kilodaltons to about 300 kilodaltons.

Non-degradable polymers can also include those described in U.S. Pat. App. No. 2007/0026037, entitled "DEVICES, ARTICLES, COATINGS, AND METHODS FOR CONTROLLED ACTIVE AGENT RELEASE OR HEMOCOMPATIBILITY", the contents of which is herein incorporated by reference. As a specific example, non-degradable polymers can include random copolymers of butyl methacrylate-co-acrylamido-methyl-propane sulfonate (BMA-AMPS). In some embodiments, the random copolymer can include AMPS in an amount equal to about 0.5 mol. % to about 40 mol. %.

The present invention may be better understood with reference to the following examples. These examples are intended to be representative of specific embodiments of the invention, and are not intended as limiting the scope of the invention.

EXAMPLES

Example 1

Parylene Coat Over Non-Degradable Hydrophobic Matrix

Poly-n-butylmethacrylate (PBMA) and polyethylene-co-vinyl acetate (PEVA) were combined in a solvent of chloroform to form a non-degradable polymer solution having 10 mg/ml PBMA and 10 mg/ml PEVA (total solids concentration of 20 mg/ml).

IgG rabbit anti-goat antibodies were obtained from Sigma-Aldrich, St. Louis, Mo. The IgG rabbit anti-goat antibodies were combined with non-specific IgG rabbit antibodies at a ration of 10:1 non-specific to specific in PBS (phosphate buffered saline) to form an IgG solution.

MP-35N alloy coils (N=7) were simultaneously coated with both the non-degradable polymer solution and the IgG solution. The non-degradable polymer solution was applied onto the exterior surface of a first ultrasonic nozzle (60 KHz ultrasonic nozzle from Sono-Tek, Milton, N.Y., operating at about 0.5 to 1.5 watts) at a rate of 0.025 mL/minute. Simultaneously, the IgG solution was applied onto the exterior surface of a second ultrasonic nozzle (60 KHz ultrasonic nozzle from Sono-Tek, Milton, N.Y., operating at about 0.5 to 1.5 watts) at a rate of 0.025 mL/minute. Both ultrasonic spray nozzles were directed at the coils. Coils were then passed back and forth under the spray nozzles and rotated a plurality of times. This treatment resulted in a coating having approximately 50 wt. % IgG, 25 wt. % PBMA, and 25 wt. % PEVA.

The total protein loading (specific and non-specific IgG) was calculated to be about 656 μg on average. The total active protein loading was calculated to be about 66 μg on average. After coating, the coils were dried in a vacuum chamber at ambient temperature for 24 hours.

Next, a layer of parylene C was vapor deposited onto two sets of coils. Specifically, for a first set (N=2) 0.5 grams of parylene C dimer (Specialty Coating Systems, Indianapolis, Ind.) was loaded into a vapor deposition system PDS-2010 LABCOTER® (Specialty Coating Systems, Indianapolis, Ind.). A coating cycle was then initiated and a layer of parylene approximately 0.1 to 0.3 microns thick was deposited onto the first set of coils under vacuum. For a second set (N=2), 1.0 gram of parylene C dimer was loaded into the vapor deposition system. A coating cycle was then initiated and a layer of parylene approximately 0.4 to 0.6 microns thick was deposited onto the second set of coils under vacuum. For a control set (N=3), no parylene was deposited.

Figure 6:
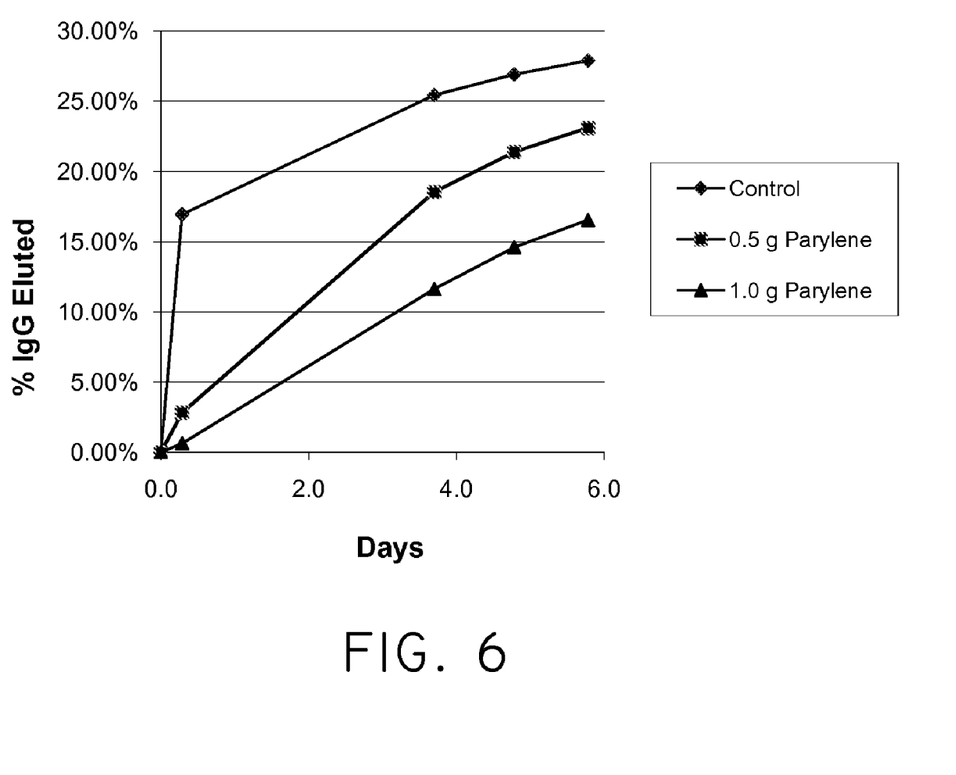
FIG. 6 is a graph showing elution of IgG from a medical device into a test solution over time.

The elution rate of the IgG antibodies from the three sets of coils was then evaluated. Coils were placed in microcentrifuge tubes in 500 μL of a solution of 1×PBS. At predetermined intervals for 63 days, 200 μL of the eluent solution was removed, divided into two 100 μL aliquots, and placed into two 96 well plates. The remaining 300 μL was removed from the microcentrifuge tube, and 0.5 mL of fresh eluent solution (1×PBS) was added to the microcentrifuge tube having the coil. The eluent samples were also analyzed for total IgG release (specific and non-specific) using the Bradford method assay (dye obtained from Sigma Chemical Co., St. Louis, Mo.). The results are shown in Table 1 below and in FIG. 6.

TABLE 1

| | Cumulative IgG Release (% of Total IgG) | | |
|---|---|---|---|
| Days | Control | 0.5 g parylene | 1.0 g parylene |
| 0 | 0.00% | 0.00% | 0.00% |
| 0.29 | 16.95% | 2.81% | 0.63% |
| 3.7 | 25.44% | 18.54% | 11.63% |
| 4.78 | 26.92% | 21.38% | 14.59% |
| 5.78 | 27.90% | 23.11% | 16.54% |

This example shows that parylene can be used as a top layer and can be made porous enough to allow for the elution of a macromolecule such as a peptide or a protein. This example further shows that the amount of parylene deposited can affect the elution rate of the resulting coating.

Example 2

Effects of Vacuum Drying on Elution Rate

Poly-n-butylmethacrylate (PBMA) and polyethylene-co-vinyl acetate (PEVA) were combined in a solvent of chloroform to form a non-degradable polymer solution having 12.5 mg/ml PBMA and 12.5 mg/ml PEVA (total solids concentration of 25 mg/ml).

IgG rabbit anti-goat antibodies were obtained from Sigma-Aldrich, St. Louis, Mo. The IgG rabbit anti-goat antibodies were combined with non-specific IgG rabbit antibodies at a ration of 10:1 non-specific to specific in PBS (phosphate buffered saline) to form an IgG solution with a concentration of 20 mg/ml of IgG.

MP-35N alloy coils (N=4) were segregated into two experimental groups (Group 1 (N=2) and Group 2 (N=4)). The non-degradable polymer solution and the IgG solution were simultaneously deposited onto the coils. Specifically, the non-degradable polymer solution was applied onto the exterior surface of a first ultrasonic nozzle (60 KHz ultrasonic nozzle from Sono-Tek, Milton, N.Y., operating at about 0.5 to 1.5 watts) at a rate of 0.04 mL/minute. Simultaneously, the IgG solution was applied onto the exterior surface of a second ultrasonic nozzle (60 KHz ultrasonic nozzle from Sono-Tek, Milton, N.Y., operating at about 0.5 to 1.5 watts) at a rate of 0.02 mL/minute. Both ultrasonic spray nozzles were directed at the coils. The coils were passed back and forth under the spray nozzles and rotated a plurality of times. This treatment resulted in a coating having approximately 40 wt. % IgG, 30 wt. % PBMA, and 30 wt. % PEVA. The total protein loading (specific and non-specific IgG) was calculated to be about 710 μg on average for the coils of Group 1 and about 685 μg on average for the coils of Group 2.

After coating with the non-degradable polymer solution and the IgG solution, the coils of Group 1 were dried in a vacuum chamber at ambient temperature for about 12-16 hours. However, the coils of Group 2 were not dried in a vacuum chamber. Rather, the coils of Group 2 were dried for the same length of time under ambient temperature and pressure conditions.

Next, a layer of parylene C was vapor deposited onto the coils of Group 1 and Group 2. Specifically, 2.0 grams of parylene C dimer (Specialty Coating Systems, Indianapolis, Ind.) was loaded into a vapor deposition system PDS-2010 LABCOTER® (Specialty Coating Systems, Indianapolis, Ind.). A coating cycle was then initiated and a layer of parylene approximately 0.8 to 1.2 microns thick was deposited onto the coils of both experimental groups. Specifically, about 59.5 μg of parylene was deposited onto the coils of Group 1 and about 57 μg of parylene was deposited onto the coils of Group 2.

Figure 7:
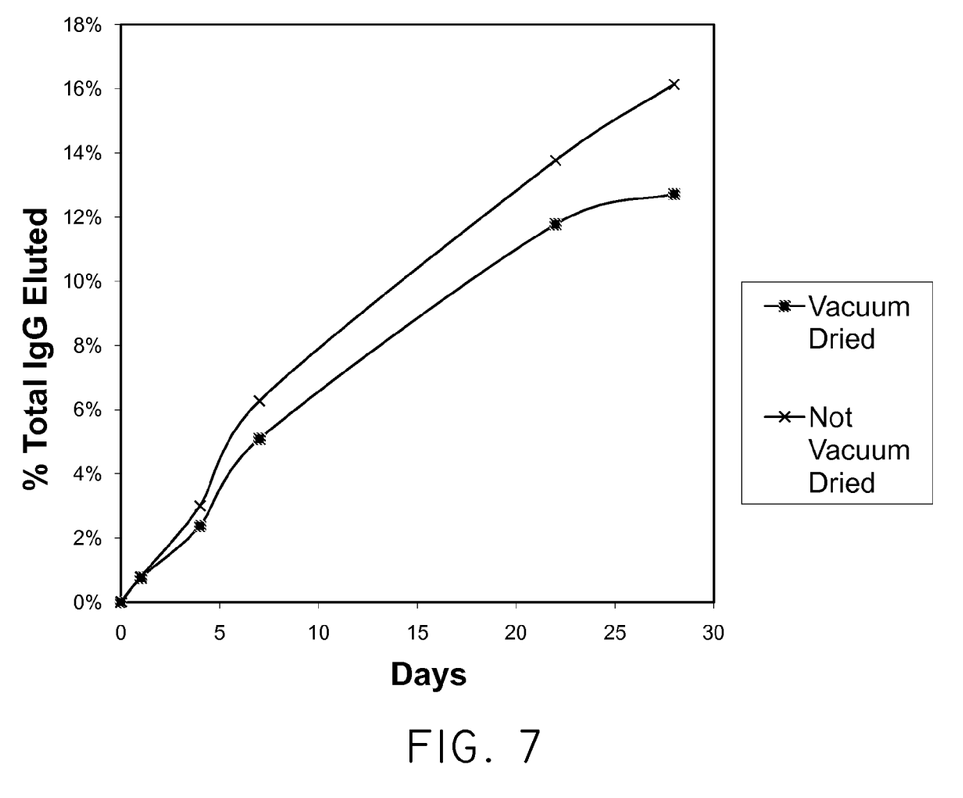
FIG. 7 is a graph showing elution of IgG from a medical device into a test solution over time.

The elution rate of the IgG antibodies from the coils of Group 1 and Group 2 was then evaluated as described above in Example 1. The results are shown below in Table 2 and in FIG. 7.

TABLE 2

| | Cumulative IgG Release (% of Total IgG) | |
|---|---|---|
| Days | Vacuum Dried | Not-Vacuum Dried |
| 0 | 0.00% | 0.00% |
| 1 | 0.76% | 0.79% |
| 4 | 2.37% | 3.00% |
| 7 | 5.09% | 6.27% |
| 22 | 11.78% | 13.77% |
| 28 | 12.72% | 16.14% |

This example shows that treatment of a material before a parylene layer is applied can affect the resulting elution rate of an active agent. Specifically, this example shows that exposing an underlying material to conditions, such as vacuum conditions, that promote vaporization of certain components before a parylene layer is applied can slow down the elution rate of an active agent from the resulting coating.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A method of applying an elution control coating to a substrate comprising:
   depositing a coating solution onto the substrate to form a base layer, the coating solution comprising an active agent, a polymer, and a solvent;
   selecting a concentration of the solvent effective to produce a coating with a desired elution rate;
   removing solvent from the base layer to obtain the selected concentration of solvent; and
   depositing a layer of parylene on the base layer while the solvent is out-gassing from the base layer to produce a porous parylene layer.

2. The method of claim 1, wherein depositing a coating solution onto the substrate to form a base layer comprises spraying a coating solution onto the substrate.

3. The method of claim 1, the active agent comprising a macromolecule.

4. The method of claim 1, the active agent selected from the group consisting of peptides and proteins.

5. The method of claim 1, the active agent selected from the group consisting of antibodies and antibody derivatives.

6. The method of claim 1, the solvent comprising a non-polar solvent.

7. The method of claim 1, the solvent comprising a polar solvent.

8. The method of claim 1, wherein depositing a coating solution onto a substrate to form a base layer comprises simultaneously spraying a first coating solution onto the substrate from a first spray head and spraying a second coating solution onto the substrate from a second spray head.

9. The method of claim 8, the first coating solution comprising the active agent and the second coating solution comprising the polymer.

10. The method of claim 8, the polymer comprising a degradable polymer and a non-degradable polymer, the first coating solution comprising the degradable polymer and the active agent and the second coating solution comprising non-degradable polymer.

11. The method of claim 1, wherein removing solvent from the base layer comprises inserting the base layer and the substrate into a vacuum chamber.

12. The method of claim 1, wherein removing solvent from the base layer comprises inserting the base layer and the substrate into a vacuum chamber for a period of time greater than about 30 minutes.

* * * * *